(12) United States Patent
Schuurhuis

(10) Patent No.: US 6,350,715 B1
(45) Date of Patent: Feb. 26, 2002

(54) PREPARATION OF AN ACTIVATED CATALYST USING AN INERT GAS IN THE ABSENCE OF HYDROGEN

(75) Inventor: Gilbert Schuurhuis, Amsterdam (NL)

(73) Assignees: Total Raffinage Distribution S.A., Puteaux (FR); Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/413,122

(22) Filed: Oct. 6, 1999

(30) Foreign Application Priority Data

Oct. 9, 1998 (EP) .............................................. 98203399

(51) Int. Cl.$^7$ ................................................ B01J 31/00
(52) U.S. Cl. ....................... 502/134; 502/234; 502/334; 502/203; 502/300; 502/303
(58) Field of Search ................................ 502/300, 325, 502/326, 327, 333, 334, 335

(56) References Cited

U.S. PATENT DOCUMENTS

| | | | |
|---|---|---|---|
| 3,449,264 A | 6/1969 | Myers | 252/441 |
| 5,151,400 A | 9/1992 | Szabo et al. | 502/203 |
| 5,591,689 A | 1/1997 | Wu et al. | 502/234 |
| 5,654,254 A | 8/1997 | Wu et al. | 502/334 |
| 5,707,918 A | * 1/1998 | Wu et al. | 502/230 |
| 5,707,921 A | 1/1998 | Wu et al. | 502/334 |

FOREIGN PATENT DOCUMENTS

| | | | |
|---|---|---|---|
| EP | 0 409 679 | 1/1991 | .......... B01J/27/135 |
| GB | 952348 | 3/1964 | |
| WO | WO 97/19752 | 6/1997 | ............ B01J/31/14 |

* cited by examiner

Primary Examiner—Helane Myers
(74) Attorney, Agent, or Firm—Louis A. Morris

(57) ABSTRACT

The invention pertains to a process for preparing an activated catalyst, to the activated catalyst composition and the use thereof in the conversion of hydrocarbon feedstocks, such as isomerisation. The catalyst composition comprising a Group VIII noble metal and a hydrocarbon-substituted aluminum compound on an alumina carrier is activated by contacting it with an inert gas in the absence of hydrogen at a temperature above 400° C., wherein at least when the hydrocarbon-substituted aluminum compound is a non-halide hydrocarbon-substituted aluminum compound, the catalyst composition is contacted with a halogen-containing gas either prior to the treatment with the inert gas or during the treatment with the inert gas, and subsequently cooling down the activated catalyst to ambient temperature in an inert gas optionally containing hydrogen or containing, at a temperature below 400° C., a halogen-containing gas; or if a halogen-containing gas is present during the treatment with the inert gas, alternatively cooling down in a mixture of an inert gas, a halogen-containing gas, and, optionally, hydrogen.

11 Claims, No Drawings

PREPARATION OF AN ACTIVATED CATALYST USING AN INERT GAS IN THE ABSENCE OF HYDROGEN

BACKGROUND OF THE INVENTION

1. Field of the Invention

The invention pertains to a process for the preparation of an activated catalyst composition, in particular an isomerisation catalyst using an inert gas in the absence of hydrogen, to the use of this activated catalyst composition for the conversion of a hydrocarbon feedstock, in particular for isomerisation, and to an activated catalyst composition obtainable by said process.

2. Description of the Prior Art

The preparation of activated isomerisation catalysts is known in the art. U.S. Pat. No. 5,654,254 describes a process in which a catalyst comprising a Group VII metal, a hydrocarbon-substituted aluminum chloride, and an alumina carrier is activated by first heating the catalyst in an inert gas atmosphere at a temperature of about 630°–750° C. and subsequently treating the resulting material with a hydrogen chloride-containing gas at a temperature of 630°–750° C. and cooling the resulting mixture in an inert gas atmosphere to ambient temperature.

The gas composition thus is changed twice in the process disclosed in U.S. Pat. No. 5,654,254, viz. from inert gas to a mixture of halogen-containing gas and inert gas and from this mixture to inert gas. Furthermore, if a halogen-containing gas is applied, excess halogen-containing gas which has not reacted with the catalyst during the activation step has to be removed via, e.g., an adsorption tower. The process of U.S. Pat. No. 5,654,254 thus is technically quite complicated. It is therefore an object of the present invention to obtain a technically simple activation process.

The halogen-containing gas is applied in U.S. Pat. No. 5,654,254 at a temperature above 630° C. At such high temperatures, halogen-containing gases have a highly corrosive effect on the process equipment. It is therefore a further object of the present invention to reduce or avoid the corrosive effect of the halogen-containing gas during the activation process.

Another reference dealing with the activation of an isomerisation catalyst optionally in the presence of a halogen-containing gas is WO 9719752. In the process described in this reference, a catalyst composition comprising a Group VIII noble metal and a hydrocarbon-substituted aluminum compound on an alumina carrier containing up to 20 wt % of other components is activated by being contacted with a hydrogen-containing gas at a temperature above 500° C., with the proviso that at least when the hydrocarbon-substituted aluminum compound present in the catalyst composition does not comprise halogen, the catalyst composition to be activated is contacted with a halogen-containing gas either prior to or during the treatment with the hydrogen-containing gas. However, though it is possible to prepare activated isomerisation catalysts with the process of this reference, there is still a need to further increase the activity of these catalysts in order to ensure highly effective hydrocarbon conversion. It is therefore another object of the present invention to prepare catalysts with high activity in hydrocarbon conversion reactions, such as the isomerisation of hydrocarbons.

Like WO 9719752, EP 0409679 deals with an activation process in which preferably hydrogen is present during the activation step and which is carried out at a temperature of 300°–475° C.

Further, GB 952,348 discloses the activation of a catalyst composition comprising a Group VIII noble metal, a non-halide hydrocarbon-substituted aluminum compound, and an alumina carrier, wherein the activation is carried out by contacting the catalyst composition with a mixture of a halogen-containing gas and an inert gas at a temperature below 260° C. (500° F.) and optionally further contacting the resulting catalyst composition with hydrogen or nitrogen, preferably hydrogen, at a temperature of 204°–371° C. (400°–700° F.), preferably 232°–343° C. (450°–650° F.).

Finally, U.S. Pat. No. 5,707,921 discloses an activation process wherein first a high temperature treatment in inert gas is carried out, subsequently a halogen-containing gas in admixture with hydrogen is applied, and finally, the resulting catalyst is cooled to room temperature in an inert gas.

Surprisingly, it has been found that the above problems can be solved and objectives achieved by the unique process of the present invention.

SUMMARY OF THE INVENTION

Accordingly, in one embodiment, the present invention is a process for preparing an activated catalyst composition which process comprises the sequential steps of (a) contacting a catalyst composition comprising a Group VIII noble metal and a hydrocarbon-substituted aluminum compound on an alumina carrier containing up to 20 wt % of other components with an inert gas in the absence of hydrogen at a temperature above 400° C., wherein at least when the hydrocarbon-substituted aluminum compound is a non-halide hydrocarbon-substituted aluminum compound, the catalyst composition is contacted with a halogen-containing gas either prior to the treatment with the inert gas or during the treatment with the inert gas, (b) cooling down to ambient temperature in an inert gas optionally containing hydrogen or containing, at a temperature below 400° C., a halogen-containing gas; or if a halogen-containing gas is present during the treatment with the inert gas, alternatively cooling down in a mixture of an inert gas, a halogen-containing gas, and, optionally, hydrogen.

In a second embodiment, the present invention comprises an activated catalyst composition obtained by the process of the first embodiment.

In a third embodiment, the present invention comprises a process for using the activated catalyst composition of the second embodiment.

Other objectives and embodiments of the present invention encompass details about catalyst compositions, reactants and reaction conditions all of which are hereinafter disclosed in the following discussion of each of the facets of the present invention.

DETAILED DESCRIPTION OF THE INVENTION

It has been found in the present invention that when activation step (a) is carried out in the presence of the inert gas and in the absence of a halogen-containing gas, the activity of the resulting catalyst is comparable to that obtained according to the process of U.S. Pat. No. 5,654,254, where an additional high-temperature halogen treatment is carried out subsequent to the treatment with the inert gas. Thus, it is possible in the process of the present invention to avoid such a high-temperature halogen treatment, while maintaining the catalyst's high activity.

Surprisingly, it has further been found in the present invention that when the halogen-containing gas is applied prior to the treatment with the inert gas, the activity of the resulting catalyst is significantly higher than when a halogen-containing gas is applied subsequent to the treatment with the inert gas as disclosed in U.S. Pat. No. 5,654,254.

Furthermore, it has surprisingly been found in the present invention that when steps (a) and (b) as described above are both carried out in the presence of a mixture of the inert gas and the halogen-containing gas, the activity of the resulting catalyst is significantly higher than that of a catalyst according to U.S. Pat. No. 5,654,254. In other words, a catalyst with an even higher activity can be obtained while, in contrast to U.S. Pat. No. 5,654,254, the gas composition remains unchanged. Thus the undesired corrosive effect resulting from the high-temperature halogen treatment in this embodiment of the present invention is compensated by the technical simplicity of the process and by a higher catalytic activity than results from the process of U.S. Pat. No. 5,654,254.

It must be noted that in the case of the isomerisation of hydrocarbon feeds, generally small amounts of halogen compounds are present in the hydrocarbon feed. These isomerisation processes are generally carried out at temperatures below 330° C. Consequently, the corrosive effect of the halogen compound in this case is much smaller than when the halogen compound is applied at high temperatures of, e.g., above 630° C., as is the case in the process of U.S. Pat. No. 5,654,254.

Finally, it has also surprisingly been found that if an inert gas is applied in the absence of hydrogen according to the present invention instead of a hydrogen-containing gas as disclosed in WO 9719752, catalyst compositions with an even higher activity than those described in WO 9719752 can be obtained.

With regard to other prior art references mentioned above, GB 952,348 does not disclose the high-temperature activation step of the present invention.

It is also noted that the process embodiment of the present invention in which hydrogen is present during cooling step (b) is clearly different from the teaching of U.S. Pat. No. 5,707,921. In the present invention a mixture of hydrogen and halogen-containing gas is only applied after prior treatment with a mixture of halogen-containing gas and inert gas, and not, as in U.S. Pat. No. 5,707,921, inert gas alone. Further, though U.S. Pat. No. 5,707,921 mentions that the catalysts to be activated may contain hydrocarbon-substituted aluminum compounds, the only catalysts exemplified in this reference contain aluminum trichloride.

Catalyst Activation Process

As has been described above, the present invention refers to a process for preparing an activated catalyst composition which process comprises the sequential steps of (a) contacting a catalyst composition comprising a Group VIII noble metal and a hydrocarbon-substituted aluminum compound on an alumina carrier containing up to 20 wt % of other components with an inert gas in the absence of hydrogen at a temperature above 400° C., wherein at least when the hydrocarbon-substituted aluminum compound is a non-halide hydrocarbon-substituted aluminum compound, the catalyst composition is contacted with a halogen-containing gas either prior to the treatment with the inert gas or during the treatment with the inert gas, (b) cooling down to ambient temperature in an inert gas optionally containing hydrogen or containing, at a temperature below 400° C., a halogen-containing gas; or if a halogen-containing gas is present during the treatment with the inert gas, alternatively cooling down in a mixture of an inert gas, a halogen-containing gas, and, optionally, hydrogen.

The present invention comprises, e.g., the following process embodiments:

(i) treatment with inert gas at a temperature above 400° C. in the absence of hydrogen, optionally after prior halogen treatment, and cooling down in inert gas, (ii) treatment with inert gas at a temperature above 400° C. in the absence of hydrogen, optionally after prior halogen treatment, and cooling down in a mixture of inert gas and hydrogen, (iii) treatment with inert gas at a temperature above 400° C. in the absence of hydrogen, optionally after prior halogen treatment, and cooling down in inert gas with a halogen-containing gas being present during the cooling step at a temperature below 400° C., (iv) treatment with a mixture of halogen-containing gas and inert gas at a temperature above 400° C. in the absence of hydrogen, and cooling down in inert gas, (v) treatment with a mixture of halogen-containing gas and inert gas at a temperature above 400° C. in the absence of hydrogen, and cooling down in a mixture of inert gas and hydrogen, (vi) treatment with a mixture of halogen-containing gas and inert gas at a temperature above 400° C. in the absence of hydrogen, and cooling down in a mixture of inert gas and halogen-containing gas, and (vii) treatment with a mixture of halogen-containing gas and inert gas at a temperature above 400° C. in the absence of hydrogen, and cooling down in a mixture of inert gas, halogen-containing gas and hydrogen.

If the hydrocarbon-substituted aluminum compound contained in the catalyst to be activated is a hydrocarbon-substituted aluminum dihalide, it is preferred that essentially no halogen-containing gas is present during activation step (a) of the process of the present invention. Further, in the case of a hydrocarbon-substituted aluminum monohalide, preferably a halogen-containing gas is present during activation step (a) either prior to or during the treatment with the inert gas. Finally, in the case of a non-halide hydrocarbon-substituted aluminum compound, a halogen-containing gas must be present during activation step (a) either prior to or during the treatment with the inert gas.

The treatment with the inert gas in step (a), optionally in the presence of a halogen-containing gas, is preferably carried out at a temperature above 500° C., more preferably at a temperature in the range of 500° to 1000° C., even more preferably in the range of 500° to 800° C., and most preferably in the range of 600° to 750° C. Generally, the isothermal time at maximum temperature is in the range of 1 second to 5 hours, preferably 15 minutes to 5 hours, and most preferably 30 minutes to 3 hours.

The inert gas used in the activation of the catalyst composition preferably is at least 90 vol %, more preferably at least 95 vol %, and most preferably at least 98 vol % of a gas selected from nitrogen, argon, helium, or mixtures thereof, with nitrogen being preferred. The inert gas preferably holds less than 10 ppm of water and less than 10 ppm of oxygen or oxygen-containing components and is substantially free of halogen and hydrogen.

As has been stated above, hydrogen must not be present during the activation step (a). This means that generally less than 10 ppm, preferably less than 5 ppm, and most preferably 0 ppm hydrogen is present during the activation step.

For good order's sake it is noted that "nitrogen" stands for nitrogen gas with the chemical formula $N_2$. Further, it is mentioned that "hydrogen" in the terms of the present invention means hydrogen gas with the chemical formula $H_2$.

When a halogen-containing gas is present during step (a) prior to the treatment with the inert gas, the halogen-containing gas preferably is present at a temperature below 500° C., and more preferably at a temperature of below 400° C., in order to at least reduce the undesired corrosive effect of the halogen-containing gas. Further, when a halogen-containing gas is present, the presence of water is preferably avoided, as the corrosive effect of a halogen-containing gas in combination with water is particularly high. The absence of water can easily be ensured by, e.g., choosing the temperature at which the halogen-containing gas is present to be at least 100° C. and preferably at least 200° C.

In the case where a halogen treatment is carried out prior to the treatment with the inert gas, the contact time with the halogen-containing gas depends, inter alia, on the temperature and the type of aluminum compound applied. Generally, the catalyst is contacted with the halogen-containing gas over a period of 0.1–5 hours, and preferably over a period of 0.5–3 hours.

Preferably, the gases applied during step (a) contain essentially no halogen-containing gas. More particularly, the amount of halogen-containing gas applied during step (a) preferably is below 10 vol %, more preferably below 5 vol %, and still more preferably below 2 vol %, based on the volume of all gases applied during step (a). Most preferably, step (a) is carried out in the complete absence of any halogen-containing gas.

As described above, cooling step (b) is, e.g., carried out in the presence of an inert gas and optionally hydrogen. Further, if so desired, a halogen-containing gas may be present during cooling step (b). However, when in step (a) no halogen-containing gas is present during the treatment with the inert gas, it is essential that the halogen-containing gas be present during the cooling step only at temperatures below 400° C. and preferably above 100° C., more preferably above 200° C.

A halogen-containing gas may be present during the cooling step at temperatures above 400° C. only when a halogen-containing gas is present also during the treatment with the inert gas. In this case steps (a) and (b) are both performed in the presence of a mixture of halogen-containing gas and inert gas.

Preferably, the gases applied during step (b) contain essentially no halogen-containing gas. More particularly, the amount of halogen-containing gas applied during step (b) preferably is below 10 vol %, more preferably below 5 vol %, and still more preferably below 2 vol %, based on the volume of all gases applied during step (b). Most preferably, step (b) is carried out in the complete absence of any halogen-containing gas.

If so desired, hydrogen may be present during cooling step (b), preferably in admixture with an inert gas. Hydrogen in admixture with a halogen-containing gas and optionally an inert gas may only be present during the cooling step when a mixture of inert gas and halogen-containing gas has been applied in activation step (a). In this case, the process of the invention can be carried out by activating the catalyst in a mixture of inert gas and halogen-containing gas and cooling the resulting catalyst in the same gas mixture under addition of hydrogen. Generally, the amount of hydrogen is chosen to be less than 5 vol %, based on the total volume of all gases present during the cooling step.

Typically, the temperature is gradually reduced to ambient temperature during cooling step (b). Generally, the cooling rate during the cooling step has little effect on the final activity of the catalyst. Cooling may, e.g., be carried out by simply turning off the heating source which was necessary during the activation step.

In another embodiment of the invention, cooling step (b) may comprise, e.g., one or more isotherms. Thus the activated catalyst composition may be gradually cooled down from the activation temperature to a temperature of, e.g., below 400° C., hold isothermally at this temperature for a certain time, and finally be gradually reduced to ambient temperature. Such a treatment is typically applied when hydrogen is present during the cooling step. E.g., after activation in inert gas, the catalyst composition may be cooled down to a temperature below 400° C. in inert gas. At this temperature hydrogen may be added, and the catalyst composition may be kept at this temperature for a time of, e.g., 1 minute to 5 hours. Subsequently, the catalyst composition may be cooled down to ambient temperature in the same mixture of hydrogen and inert gas.

For good order's sake, it is noted that "ambient temperature" in the sense of the present invention typically means a temperature in the range of 20°–30° C., such as 25° C.

It is noted that the process of the present invention preferably consists essentially of steps (a) and (b) described above. This means in particular that any process steps which do not lead to an increase in the activity of the resulting catalyst or even reduce it are preferably avoided. It is further preferred that both step (a) and step (b) are carried out in the complete absence of any halogen-containing gas and of hydrogen.

Preferably, the gas composition in the process of the present invention is changed not more than twice. More preferably, it is changed not more than once and most preferably, steps (a) and (b) of the present invention are carried out in one and the same gas composition.

A process wherein the gas composition is not changed can be realised, e.g., by carrying out steps (a) and (b) both in the same inert gas in the absence of hydrogen and in the absence of a halogen-containing gas, or by carrying out both steps in the same mixture of an inert gas and a halogen-containing gas in the absence of hydrogen.

Typically, a process wherein the gas composition is changed once can be realised by, e.g., first contacting the catalyst to be activated with a halogen-containing gas and subsequently contacting it with an inert gas at high temperature and cooling down in the same inert gas, or by performing step (a) in an inert gas without prior halogen treatment and cooling down in a mixture of an inert gas and hydrogen.

Finally, a process where the gas composition is changed twice might typically consist of the subsequent steps of a halogen treatment, a high temperature treatment in an inert gas, and cooling down in a mixture of inert gas and hydrogen.

If an inert gas is applied in both process steps, the inert gas may be changed during the process. E.g., activation step (a) may be carried out in nitrogen and cooling step (b) may be carried out in argon. The same holds for when a halogen-containing gas is applied in both process steps. For good order's sake, it is noted that the change from one inert gas to another or from one halogen-containing gas to another is also a change in gas composition in the sense of the present invention. Incidentally, a change in inert gas generally is less preferred.

In the processes where a hydrocarbon-substituted aluminum halide comprises the catalyst composition to be activated, the hydrocarbon-substituted aluminum halide may be, e.g., a compound satisfying the formula $AlX_yR1_nR2_m$, wherein X is a halogen atom, R1 and R2 may be the same or different and are selected from alkyl groups or aryl groups having 1–12 carbon atoms, y has the value 1 or 2, and n and m have the value 0 or 1, with the sum of y, n, and m being 3. X may be selected from fluorine, chlorine, bromine, and iodine, and is preferably chlorine. R1 and R2 may be selected from, e.g., methyl, ethyl, isopropyl, butyl, phenyl, cyclohexyl, etc. It is preferred that the hydrocarbon substituted aluminum halide is a hydrocarbon-substituted aluminum chloride. Suitable hydrocarbon-substituted aluminum chlorides include diethyl aluminum chloride, methyl aluminum dichloride, ethyl aluminum dichloride, and isobutyl aluminum dichloride. It should be noted that the hydrocarbon-substituted aluminum halide also may be a mixture of various hydrocarbon-substituted aluminum halides or a complex, for instance an alkyl aluminum sesquichloride.

In the process where a non-halide hydrocarbon-substituted aluminum compound is comprised in the catalyst composition to be activated, the non-halide hydrocarbon-substituted aluminum compound may, e.g., satisfy the formula AlR1R2R3, wherein R1, R2, and R3 may be the same or different and are selected from alkyl groups or aryl groups having 1–12 carbon atoms, such as described above. Examples of hydrocarbon-substituted aluminum compounds include triethyl aluminum and isobutyl diethyl aluminum. Mixtures of various non-halide hydrocarbon-substituted aluminum compounds may also be used.

If so desired, the catalyst composition to be activated may also comprise a combination of one or more hydrocarbon-substituted aluminum halides with one or more non-halide hydrocarbon-substituted aluminum compounds. In that case, if desired, additional halogen may be incorporated into the catalyst composition by contacting the catalyst composition with a halogen-containing gas either prior to the treatment with the inert gas, or during the treatment with the inert gas as described above.

In any case, care should be taken that a sufficient amount of halide is added to the catalyst composition. The final catalyst will generally contain 0.2–15 wt % of halogen, preferably chlorine, based on the total weight of the final catalyst. Preferably, the final catalyst of the invention has a halogen content of at least 2.5 wt %, more preferably of at least 3.0 wt %, and even more preferably of at least 3.5 wt %, based on the total weight of the catalyst. The required halogen content of the final catalyst can be obtained by a proper selection of the amount of hydrocarbon-substituted aluminum halide and/or of the amount of halogen contained in the halogen-containing gas applied prior to or during the treatment with the inert gas.

In processes where a halogen-treatment is carried out, halogen-containing gases such as hydrogen chloride, a halogen gas, such as $C_{12}$, a halogenated hydrocarbon, such as carbon tetrachloride, chloroform, chloroethane can be applied. Hydrogen halides, particularly HCl, generally are preferred. If a halogen-containing gas is applied, this is preferably done in admixture with an inert gas. Preferably, the molar ratio of the halogen contained in the halogen-containing gas to the inert gas is in the range of 0.1 to 10, more particularly in the range of 1 to 5. It is noted that the term "halogen-containing gas" in the sense of the present invention means a halogen-containing gas added during the process of the present invention. Minor amounts of halogen-containing gases arising from, e.g., degradation of the hydrocarbon-substituted aluminum halide are not encompassed by the term "halogen-containing gas."

The catalyst composition to be activated is described in detail as follows: The Group VIII noble metal present in the catalyst composition may be selected from the group of ruthenium, rhenium, palladium, osmium, iridium, and platinum, with preference being given to platinum, palladium, and mixtures thereof. The final catalyst preferably contains 0.01–2 wt % of the Group VIII noble metal, calculated as metal, more particularly 0.05 to 1 wt %. Other metal components may also be present in the catalyst composition if so desired. Examples of other metal components which may influence the activity, selectivity or stability of the catalyst are tin, lead, germanium, bismuth, cobalt, nickel, indium, gallium, zinc, uranium, thallium, zirconium, and mixtures thereof.

The alumina carrier containing up to 20 wt % of other components preferably takes the form of particles, which are obtained by means of, e.g., extrusion, pelletizing, or by some other known method. The particles' shape may vary. As suitable shapes may be mentioned spheres, cylinders, rings, and symmetric or asymmetric polylobes, such as trilobes and quadrulobes. Generally, the particles will have a diameter in the range of 1 to 10 mm, and a length which is also in the range of 1 to 10 mm. The alumina may contain up to 20 wt % of other constituents, such as silica, magnesia, titania, or zirconia. It is preferred that more than 90 wt % of the carrier, more preferably over 95 wt %, and most preferably substantially the entire carrier consists of alumina. Here, the term "substantially all" means that the catalyst carrier consists essentially of alumina, with the only additional carrier components being impurities of which the presence is unavoidable. Suitable aluminas include the active aluminas such as gamma-alumina, eta-alumina, theta-alumina, and mixtures thereof. Gamma-alumina is particularly preferred.

The alumina carrier containing up to 20 wt % of other components preferably has a B.E.T. surface area of 100–500 $m^2/g$, a total pore volume of 0.1–1 ml/g (determined by mercury porosimetry with a contact angle of 140°), and an average pore diameter of 2–20 nm.

The preparation of the catalyst composition to be activated is described in detail as follows:

The catalyst composition to be activated is generally prepared by a process in which the following successive steps are carried out:

(i) the preparation of a composition comprising the Group VII noble metal and the alumina carrier containing up to 20 wt % of other components, (ii) the optional reduction of the noble metal, and (iii) the contacting of the product of step (i) or (ii) with the hydrocarbon-substituted aluminum compound.

The compositing of the metal components with the carrier may be carried out in any manner known in the art. For example, one can start by preparing carrier particles by shaping a carrier precursor, for example by extrusion, and calcining the resulting shaped particles. The carrier particles can then be impregnated with an impregnating solution comprising a soluble salt or complex of the metal or metals to be provided. For example, one may impregnate the carrier with an impregnation solution containing chloroplatinic acid, platinum dichloride, platinum tetrachloride hydrate, etc. It is well-known in the art to add additional components to the impregnation solution to stabilise the solution, or to influence the distribution of metal over the catalyst carrier. For example, if a homogeneous platinum distribution is desired, a strongly acid impregnation solution, such as an impregnation solution containing chloroplatinic acid, HCl, and $HNO_3$, is commonly used. The impregnated particles may optionally be calcined.

On the other hand, it is also possible to mix compounds of the metal or metals to be incorporated into the catalyst composition with the carrier precursor, and then shape the mixture, for example by extrusion, after which the extrudates are calcined. If so desired, the Group VII metal component present on the carrier may be reduced, e.g., by passing hydrogen over the composition at a temperature in the range of 100° to 600° C.

The hydrocarbon-substituted aluminum compound, i.e., the hydrocarbon-substituted aluminum halide and/or the non-halide hydrocarbon-substituted aluminum compound can be incorporated into the catalyst composition in an amount of 0.05 to 0.20 mole of hydrocarbon-substituted aluminum compound per mole of carrier. The hydrocarbon-substituted aluminum compound is incorporated into the catalyst composition in a manner known in the art. For example, it is possible to incorporate the hydrocarbon-substituted aluminum compound into the catalyst composition by contacting it with a composition comprising a Group VII noble metal, optionally in the reduced form, on an alumina carrier containing up to 20 wt % of other components. Although less preferred, it is also possible to first incorporate the hydrocarbon substituted aluminum compound into the catalyst composition, and only then incorporate the Group VIII noble metal.

The incorporation of the hydrocarbon-substituted aluminum compound into the catalyst composition may take the form of the compound being dissolved in a solvent and impregnating the carrier, which optionally comprises the Group VII noble metal component, with this solution, followed by removal of the solvent. Preferably, the boiling point of the solvent will not be too high, since it is harder to remove high-boiling solvents from the composition. Suitable solvents include pentane, hexane, heptane, etc. It should be noted in this context that the removal of the solvent from the solution prior to the activating step is not always required. One possible alternative is to evaporate the solvent during the activating step. Of course, the feasibility of this option is dependent upon the nature of the solvent and the other process conditions.

Preferably, during the preparation of the catalyst to be activated, any halogen treatment above 500° C. and more preferably any halogen treatment above 400° C. is avoided. Still more preferably, no halogen treatment is carried out at all during the preparation of the catalyst. "Halogen treatment" in the sense of the present invention means the contacting of the catalyst (precursor) with a halogen-containing gas.

Conversion Process

The invention further relates to the use of the activated catalyst composition obtained by the process described above for the conversion of hydrocarbon feeds.

Preferably, the activated catalyst composition is contacted with the hydrocarbon feed directly after the activation of the catalyst composition according to steps (a) and (b) as described above. "Directly" in this context means that there is no additional process step subsequent to step (b) and prior to contacting the hydrocarbon feed with the activated catalyst composition. In any case, a halogen treatment such as described in U.S. Pat. No. 5,654,254 must not be carried out subsequent to steps (a) and (b).

The conversion process of the invention preferably comprises isomerisation, alkylation, or hydrodecyclisation of the hydrocarbon feed and more preferably comprises isomerisation or alkylation of the hydrocarbon feed and most preferably comprises isomerisation of the hydrocarbon feed. If the conversion process comprises the isomerisation of a hydrocarbon feed, preferably, a feed containing n-paraffins is applied. More particularly, the feed preferably comprises aromatic and aliphatic hydrocarbons and even more preferably it comprises aromatic and aliphatic hydrocarbons having 4 to 12 carbon atoms. The feed can also comprise mixtures of different n-paraffins or mixtures of n-paraffins and aromatic hydrocarbons. The isomerisation process of the invention preferably comprises $C_4$, $C_5/C_6$, and $C_7$ isomerisations. Preferably, the feedstock to be isomerised contains at least 50 wt % of paraffins to be isomerised. The feedstock may contain olefins, but preferably less than 10%, because the presence of olefins leads to increased hydrogen consumption. As is known in the art, the feed should be relatively free of sulphur components and water, because these materials act as catalyst poisons. The feed generally contains up to 1 ppm of sulphur and up to 0.5 ppm of water.

The isomerisation process may take the form of the feed to be isomerised being contacted with the activated catalyst composition in a fixed bed at a temperature in the range of 80° to 330° C., preferably of 100° to 200° C., in the presence of hydrogen. The pressure in the isomerisation reactor generally is in the range of 1 to 60 bar, preferably of 2 to 40 bar, with the LHSV ranging from 0.5 to 40 $h^{-1}$, preferably from 1 to 20 $h^{-1}$, and the molar ratio between the hydrogen and the feed being in the range of 0.005 to 10, preferably in the range of 0.01 to 5. As those skilled in the art will know, if so desired, a minute amount of a halogen-containing compound may be incorporated into the feed in order to extend the life of the catalyst. Thus, 0.001 to 1 wt %, calculated as halogen, of a hydrogen halide, a halogen gas, or a halogenated hydrocarbon, such as carbon tetrachloride, chloroform, chloroethane, chloroisopropane, etc., may be added to the feed.

In addition, the conversion process of the invention comprises the alkylation of alkylatable aromatic or aliphatic hydrocarbons by contacting the compound to be alkylated with an alkylating agent at a suitable temperature and pressure in the presence of the activated catalyst composition. Alkylating reactions are known to those skilled in the art and require no further elucidation here.

The invention will be further illustrated by the following examples:

EXAMPLE 1

(i) Preparation of the Catalyst to be Activated

A calcined platinum-impregnated alumina carrier was prepared as described in Example 1 of WO 9719752. The resulting calcined catalyst precursor had a platinum content of 0.28 wt % and a chlorine content of 1.0 wt %. 1330 g of the calcined catalyst precursor were charged to a fixed bed unit. 1.3 g ethyl aluminum dichloride (as a 20 wt % solution in heptane) per gram of precursor were added in 30 minutes. Subsequently, the resulting mixture was heated within 15 minutes to 90°–95° C. and the temperature was kept at 90°–95° C. for 15 minutes. During this procedure, nitrogen was passed over the mixture. Next, the liquid was drained off and the resulting solid was dried with hot nitrogen having a temperature of 140° C. for approximately 115 minutes.

(ii) Activation Procedure 330 g of the catalyst resulting from step (i) were heated in a 2000 ml/min nitrogen flow to 650° C. with a heating-up rate of 8° C./min. When this temperature was reached, the catalyst was kept at this temperature under nitrogen flow (2000 ml/min) for 1 hour. Subsequently, the catalyst was cooled down to ambient temperature under nitrogen flow (2000 ml/min).

(iii) Catalytic Testing 10 g of the catalyst obtained in step (ii) were charged to a test reactor with air and moisture being excluded. The temperature was raised to approximately 145° C. under a hydrogen flow of 35 nL/hour at 30 bar. While keeping the pressure at 30 bar, after approximately one hour, oil was passed over the catalyst. The hydrogen/oil molar ratio was 3. The oil feed was composed of approximately 42 wt % n-pentane, approximately 48 wt % n-hexane, approximately 10 wt % cyclohexane, and 300 ppm Cl in the form of $CCl_4$. The initial space velocity ("WHSV") was 4 g feed (oil/$H_2$) per of gram catalyst per hour ("4 g/g/h"). This velocity was maintained for about 9 hours. After this, the space velocity was increased to 6 g/g/h and kept at this value for 4 hours and subsequently increased further to 8 g/g/h and kept at this value for 4 hours.

The relative activity of the activated catalyst was determined to be 146%. The activated catalyst had a chlorine content (calculated as Cl) of 5.1 wt %.

COMPARATIVE EXAMPLE A

A catalyst was prepared as described in step (i) of Example 1. This catalyst was activated as described in U.S. Pat. No. 5,654,254.

330 g of the catalyst were heated in a 2000 ml/min nitrogen flow to 650° C. with a heating-up rate of 8° C./min. When this temperature was reached, the gas composition was changed at constant gas flow to a mixture of 25 vol % HCl and 75 vol % nitrogen, and the catalyst was kept under this atmosphere at a gas flow of 2000 ml/min for 1 hour. Subsequently, the catalyst was cooled down to ambient temperature under nitrogen flow (2000 ml/g). The only difference between step (ii) of Example 1 according to the invention and Comparative Example A according to U.S. Pat. No. 5,654,254 thus is that in the Comparative Example the isothermal treatment at 650° C. was carried out in a mixture of HCl and nitrogen instead of in nitrogen as in Example 1.

The resulting catalyst was tested according to step (iii) of Example 1 and the relative activity was determined to be 153%. The activated catalyst had a chlorine content (calculated as Cl) of 4.9 wt %.

Thus, the relative activities of the catalyst obtained in Example 1 according to the invention and that of Comparative Example A obtained according to U.S. Pat. No. 5,654,254 are approximately the same, even though in Example 1 the high-temperature halogen treatment was not employed.

COMPARATIVE EXAMPLE B

A catalyst was prepared as described in step (i) of Example 1. This catalyst was activated as described in WO 9719752.

330 g of the catalyst were heated in a mixture of 95 vol % nitrogen and 5 vol % hydrogen at a gas flow of 2000 ml/min to 650° C. with a heating-up rate of 8° C./min. When this temperature was reached, the catalyst was kept at it under the same atmosphere (gas flow: 2000 ml/min) for 1 hour. Subsequently, the catalyst was cooled down to ambient temperature under nitrogen flow (2000 ml/min).

The only difference between Comparative Example B according to WO 9719752 and Example 1 of the present invention thus is that hydrogen was present during the activation step.

The resulting catalyst was tested according to step (iii) of Example 1 and had a relative activity of only 91%, which is significantly lower than the activity of the catalyst obtained in Example 1. The activated catalyst had a chlorine content (calculated as Cl) of 4.9 wt %.

EXAMPLE 2

A catalyst was prepared as described in step (i) of Example 1 except that diethyl aluminum monochloride was used instead of the ethyl aluminum dichloride of Example 1. 330 g of the resulting catalyst were heated in a mixture of 25 vol % HCl and 75 vol % nitrogen at a gas flow of 2000 ml/min to 650° C. with a heating-up rate of 3° C./min. When this temperature was reached, the catalyst was kept at it under the same atmosphere (2000 ml/min) for 1 hour. Subsequently, the catalyst was cooled down to ambient temperature under nitrogen flow (2000 ml/min).

The activated catalyst was tested according to step (iii) of Example 1 and the relative activity of the activated catalyst was determined to be 131%. The activated catalyst had a chlorine content (calculated as Cl) of 4.9 wt %.

EXAMPLE 3

A catalyst was prepared as described in Example 2. 330 g of the resulting catalyst were heated in a mixture of 25 vol % HCl and 75 vol % nitrogen at a gas flow of 2000 ml/min to 200° C. with a heating-up rate of 3° C./min. When this temperature was reached, the heating of the catalyst continued with 3° C./min to 650° C. in 2000 ml/min nitrogen flow. Having reached this temperature, the catalyst was kept under nitrogen flow (2000 ml/min) for one hour. Subsequently, the catalyst was cooled down to ambient temperature under nitrogen flow (2000 ml/min).

The activated catalyst was tested according to step (iii) of Example 1 and the relative activity of the resulting catalyst was determined to be 118%. The activated catalyst had a chlorine content (calculated as Cl) of 4.9 wt %.

COMPARATIVE EXAMPLE C

A catalyst was prepared as described in Example 2. Subsequently the resulting catalyst was activated according to U.S. Pat. No. 5,654,254. 330 g of the resulting catalyst were heated in a 2000 ml/min nitrogen flow to 650° C. with a heating-up rate of 3° C./min. When this temperature was reached, the gas composition was changed at constant gas flow to a mixture of 25 vol % HCl and 75 vol % nitrogen, and the catalyst was kept under this atmosphere at a gas flow of 2000 ml/min for 1 hour. Subsequently, the catalyst was cooled down to ambient temperature under nitrogen flow (2000 ml/g).

The resulting catalyst was tested according to step (iii) of Example 1 and had a relative activity of 94%, which is significantly lower than the relative activity obtained in both Example 2, where the entire activation step is carried out in a $HCl/N_2$ atmosphere, and Example 3, where a halogen treatment is carried out at low temperatures only prior to the treatment with nitrogen. The chlorine content (calculated as Cl) of the activated catalyst was 4.8 wt %.

Determination of the Isomerisation Activity

First, the total isomerisation numbers ("TIN") of the catalyst to be tested were determined for two different space velocities (6 g/g/h and 8 g/g/h). The concentrations of 2,2 dimethylbutane ("[2,2 dimethylbutane]"), all $C_6$ hydrocarbons ("total $C_6$"), isopentane ("$iC_5$"), and all $C_5$ hydrocarbons ("total $C_5$") were measured in the product oil after the space velocity WHSV had been kept at 6 g/g/h for 80 minutes (see step (iii) of Example 1). From these concentrations, the total isomerisation number TIN at a space velocity WHSV=6 g/g/h was determined for the catalyst to be tested ("$TIN^{testcat}_{6g/g/h}$")

according to the following formula:

$$TIN^{testcat}_{6g/g/h} = \frac{[2,2\text{dimethylbutane}]}{\text{total } C_6} + \frac{iC_5}{\text{total } C_5}$$

Subsequently, the same concentrations were measured in the product oil obtained after the space velocity WHSV had been kept at 8 g/g/h for 80 minutes (see step (iii) of Example 1). From these values the TIN at a WHSV of 8 g/g/h was determined in a procedure analogous to that described above for a WHSV of 6 g/g/h ("$TIN^{testcat}_{8g/g/h}$").

Second, the TIN numbers were determined for a reference catalyst as described above ("$TIN^{refcat}_{6g/g/h}$" and "$TIN^{refcat}_{8g/g/h}$").

The corresponding values were 67.9

("$TIN^{refcat}_{6g/g/h}$") and 56 ("$TIN^{refcat}_{8g/g/h}$").

From these four TIN values, the average TIN ("$TIN_{average}$") was determined.

Assuming there is a linear relationship between the TIN numbers of each catalyst and the space velocity, the space velocities at $TIN_{average}$ were determined for the catalyst to be tested and the reference catalyst.

The relative activity in per cent is then calculated as the ratio of the thus-obtained space velocity of the catalyst to be tested multiplied by 100 and that of the reference catalyst.

What is claimed is:

1. A process for preparing an activated catalyst composition which process comprises the sequential steps of
    (a) contacting a catalyst composition comprising a Group VII noble metal and a hydrocarbon-substituted aluminum compound on an alumina carrier containing up to 20 wt % of other components with an inert gas in the absence of hydrogen at a temperature above 400° C., wherein at least when the hydrocarbon-substituted aluminum compound is a non-halide hydrocarbon-substituted aluminum compound, the catalyst composition is contacted with a halogen-containing gas either prior to the treatment with the inert gas or during the treatment with the inert gas, and
    (b) cooling down to ambient temperature in an inert gas optionally containing hydrogen or containing, at a temperature below 400° C., a halogen-containing gas; or if a halogen-containing gas is present during the treatment with the inert gas, alternatively cooling down in a mixture of an inert gas, a halogen-containing gas, and, optionally, hydrogen.

2. The process of claim 1 wherein said hydrocarbon-substituted aluminum compound is a non-halide or mono-halide hydrocarbon-substituted aluminum compound and the catalyst composition is contacted with a halogen-containing gas either prior to the treatment with the inert gas or during the treatment with the inert gas.

3. The process of claim 1 wherein the hydrocarbon-substituted aluminum compound is a hydrocarbon-substituted aluminum dihalide, and wherein the entire process is carried out in the absence of a halogen-containing gas.

4. The process of claim 2 wherein the catalyst composition is contacted with a halogen-containing gas prior to the treatment with the inert gas at a temperature below 500° C.

5. The process of claim 1 wherein the catalyst composition to be activated is contacted with the inert gas in (a) at a temperature above 500° C.

6. The process of claim 1 wherein the inert gas comprises at least 90 vol % of a gas selected from nitrogen, argon, helium, or mixtures thereof.

7. The process of claim 1 wherein the catalyst composition contains platinum as Group VIII noble metal.

8. The process of claim 1 wherein the hydrocarbon-substituted aluminum halide is a hydrocarbon-substituted aluminum chloride.

9. The process of claim 1 wherein the hydrocarbon-substituted aluminum halide is a compound of the formula $AlX_yR1_nR2_m$, wherein X is a halogen atom, R1 and R2 may be the same or different and are selected from alkyl groups and aryl groups having 1 to 12 carbon atoms, y has the value 1 or 2, and n and m have the value 0 or 1, with the sum of y, n, and m being 3.

10. The process of claim 1 wherein said hydrocarbon-substituted aluminum compound is a non-halide and satisfies the formula AlR1R2R3, wherein R1, R2, and R3 may be the same or different and are selected from alkyl groups or aryl groups having 1 to 12 carbon atoms.

11. An activated catalyst composition obtained by the process of claim 2.

* * * * *